United States Patent
Hunt et al.

(10) Patent No.: US 10,953,162 B1
(45) Date of Patent: Mar. 23, 2021

(54) TAMPER EVIDENT CLOSURE ASSEMBLY

(71) Applicants: Timothy Brandon Hunt, Hollywood, FL (US); Jonathan J. Vitello, Ft. Lauderdale, FL (US)

(72) Inventors: Timothy Brandon Hunt, Hollywood, FL (US); Jonathan J. Vitello, Ft. Lauderdale, FL (US)

( * ) Notice: Subject to any disclaimer, the term of this patent is extended or adjusted under 35 U.S.C. 154(b) by 547 days.

(21) Appl. No.: 15/856,714

(22) Filed: Dec. 28, 2017

Related U.S. Application Data

(60) Provisional application No. 62/439,538, filed on Dec. 28, 2016.

(51) Int. Cl.
*A61M 5/50* (2006.01)
*A61M 5/32* (2006.01)

(52) U.S. Cl.
CPC ........ *A61M 5/5086* (2013.01); *A61M 5/3202* (2013.01)

(58) Field of Classification Search
CPC ........ A61M 5/5086; A61M 2005/3104; A61M 2005/312; A61M 2005/3106; A61M 39/02
See application file for complete search history.

(56) References Cited

U.S. PATENT DOCUMENTS

| | | |
|---|---|---|
| 732,662 A | 6/1903 | Smith |
| 1,678,991 A | 7/1928 | Marschalek |
| 1,970,631 A | 8/1934 | Sherman |
| 2,477,598 A | 8/1949 | Hain |
| 2,739,590 A | 3/1956 | Yochem |
| 2,823,674 A | 2/1958 | Yochem |
| 2,834,346 A | 5/1958 | Adams |
| 2,875,761 A | 3/1959 | Helmer et al. |
| 2,888,015 A | 5/1959 | Hunt |
| 2,952,255 A | 9/1960 | Hein, Jr. |
| 3,122,280 A | 2/1964 | Goda |
| 3,245,567 A | 4/1966 | Knight |
| 3,323,798 A | 6/1967 | Miller |
| 3,364,890 A | 1/1968 | Andersen |
| 3,368,673 A | 2/1968 | Johnson |

(Continued)

FOREIGN PATENT DOCUMENTS

| | | |
|---|---|---|
| EP | 0148116 A | 7/1985 |
| WO | WO 2008/000279 | 1/2008 |
| WO | WO 2017086607 | 5/2015 |

*Primary Examiner* — Laura A Bouchelle
(74) *Attorney, Agent, or Firm* — Malloy & Malloy, P.L.; Jennie S. Malloy

(57) ABSTRACT

A tamper evident closure structured for attachment to a connector of a medical device including an end cap, and a tip cap disposed within the end cap in an operative position. An indicator member is removably connected to the end cap. A cover is connected to the end cap and includes an access opening dimensioned to allow the connector of the medical device to be positioned therein, into attachment with said tip cap. Cooperative dimensioning between the periphery of the access opening and the outer surface of the connector results in an engagement therebetween and a closure and the access opening when the connector is disposed there-through into attachment with the tip cap. A twisting or rotation of the tip cap in a single direction, within the end cap results in disconnection of the indicator member from the end cap, thereby providing an indication of tampering.

20 Claims, 5 Drawing Sheets

(56) References Cited

U.S. PATENT DOCUMENTS

| | | |
|---|---|---|
| 3,598,120 A | 8/1971 | Mass |
| 3,610,241 A | 10/1971 | LeMarie |
| 3,700,215 A | 10/1972 | Hardman et al. |
| 3,706,307 A | 12/1972 | Hasson |
| 3,712,749 A | 1/1973 | Roberts |
| 3,747,751 A | 4/1973 | Miller et al. |
| 3,872,867 A | 3/1975 | Killinger |
| 3,904,033 A | 9/1975 | Haerr |
| 3,905,375 A | 9/1975 | Toyama |
| 3,937,211 A | 2/1976 | Merten |
| 4,005,739 A | 2/1977 | Winchell |
| 4,043,334 A | 8/1977 | Brown et al. |
| 4,046,145 A | 9/1977 | Choksi et al. |
| 4,068,696 A | 1/1978 | Winchell |
| 4,216,585 A | 8/1980 | Hatter |
| 4,216,872 A | 8/1980 | Bean |
| 4,244,366 A | 1/1981 | Raines |
| 4,252,122 A | 2/1981 | Halvorsen |
| 4,271,972 A | 6/1981 | Thor |
| 4,286,591 A | 9/1981 | Raines |
| 4,286,640 A | 9/1981 | Knox et al. |
| 4,313,539 A | 2/1982 | Raines |
| 4,369,781 A | 1/1983 | Gilson et al. |
| 4,420,085 A | 12/1983 | Wilson et al. |
| 4,430,077 A | 2/1984 | Mittleman et al. |
| 4,457,445 A | 7/1984 | Hanks et al. |
| D277,783 S | 2/1985 | Beck |
| 4,521,237 A | 6/1985 | Logothetis |
| 4,530,697 A | 7/1985 | Kuhlemann et al. |
| 4,571,242 A | 2/1986 | Klein et al. |
| 4,589,171 A | 5/1986 | McGill |
| 4,664,259 A | 5/1987 | Landis |
| 4,667,837 A | 5/1987 | Vitello et al. |
| 4,676,530 A * | 6/1987 | Nordgren ............ A61M 39/10 138/89 |
| 4,693,707 A | 9/1987 | Dye |
| 4,726,483 A | 2/1988 | Drozd |
| 4,743,229 A | 5/1988 | Chu |
| 4,743,231 A | 5/1988 | Kay et al. |
| 4,760,847 A | 8/1988 | Vaillancourt |
| 4,813,564 A | 3/1989 | Cooper et al. |
| 4,832,695 A | 5/1989 | Rosenberg et al. |
| 4,834,706 A | 5/1989 | Beck et al. |
| 4,842,592 A | 6/1989 | Caggiani et al. |
| 4,844,906 A | 7/1989 | Hermelin et al. |
| 4,906,231 A | 3/1990 | Young |
| 4,919,285 A | 4/1990 | Roof et al. |
| 4,936,445 A | 6/1990 | Grabenkort |
| 5,009,323 A | 4/1991 | Montgomery et al. |
| 5,049,129 A | 9/1991 | Zdeb et al. |
| 5,051,093 A | 10/1991 | Clegg et al. |
| D323,392 S | 1/1992 | Byrne |
| 5,135,496 A | 8/1992 | Vetter et al. |
| 5,165,560 A | 11/1992 | Ennis, III et al. |
| 5,230,429 A | 7/1993 | Etheredge, III |
| 5,267,983 A | 12/1993 | Oilschlager et al. |
| 5,292,308 A | 3/1994 | Ryan |
| 5,293,993 A | 3/1994 | Yates, Jr. et al. |
| 5,295,599 A | 3/1994 | Smith |
| 5,312,367 A | 5/1994 | Nathan |
| 5,312,368 A | 5/1994 | Haynes |
| 5,328,466 A | 7/1994 | Denmark |
| 5,328,474 A | 7/1994 | Raines |
| 5,356,380 A | 10/1994 | Hoekwater et al. |
| 5,380,295 A | 1/1995 | Vacca |
| 5,405,339 A | 4/1995 | Kohnen et al. |
| 5,456,668 A | 10/1995 | Ogle, II |
| 5,458,580 A | 10/1995 | Hajishoreh |
| 5,468,224 A | 11/1995 | Souryal |
| 5,531,695 A | 7/1996 | Swisher |
| 5,540,666 A | 7/1996 | Barta et al. |
| 5,549,571 A | 8/1996 | Sak |
| 5,558,648 A | 9/1996 | Shields |
| 5,584,817 A | 12/1996 | van den Haak |
| 5,588,239 A | 12/1996 | Anderson |
| 5,624,402 A | 4/1997 | Imbert |
| 5,674,209 A | 10/1997 | Yarger |
| 5,695,470 A | 12/1997 | Roussigne et al. |
| 5,700,247 A | 12/1997 | Grimard et al. |
| 5,702,374 A | 12/1997 | Johnson |
| 5,713,485 A | 2/1998 | Liff et al. |
| 5,776,124 A | 7/1998 | Wald |
| 5,785,691 A | 7/1998 | Vetter et al. |
| 5,797,885 A | 8/1998 | Rubin |
| 5,807,343 A | 9/1998 | Tucker et al. |
| D402,766 S | 12/1998 | Smith et al. |
| 5,883,806 A | 3/1999 | Meador et al. |
| 5,884,457 A | 3/1999 | Ortiz et al. |
| 5,902,269 A | 5/1999 | Jentzen |
| 5,951,522 A | 9/1999 | Rosato et al. |
| 5,951,525 A | 9/1999 | Thorne et al. |
| 5,954,657 A | 9/1999 | Rados |
| 5,957,166 A | 9/1999 | Safabash |
| 5,963,136 A | 10/1999 | O'Brien |
| 5,989,227 A | 11/1999 | Vetter et al. |
| 5,993,437 A | 11/1999 | Raoz |
| 6,000,548 A | 12/1999 | Tsals |
| D419,671 S | 1/2000 | Jansen |
| 6,021,824 A | 2/2000 | Larsen et al. |
| 6,027,482 A | 2/2000 | Imbert |
| 6,068,614 A | 5/2000 | Kimber et al. |
| D430,293 S | 8/2000 | Jansen |
| D431,864 S | 10/2000 | Jansen |
| 6,126,640 A | 10/2000 | Tucker et al. |
| 6,190,364 B1 | 2/2001 | Imbert |
| 6,193,688 B1 | 2/2001 | Balestracci et al. |
| 6,196,593 B1 | 3/2001 | Petrick et al. |
| 6,196,998 B1 | 3/2001 | Jansen et al. |
| 6,235,376 B1 | 5/2001 | Miyazaki et al. |
| 6,280,418 B1 | 8/2001 | Reinhard et al. |
| 6,287,671 B1 | 9/2001 | Bright et al. |
| 6,322,543 B1 | 11/2001 | Singh et al. |
| 6,338,200 B1 | 1/2002 | Baxa et al. |
| 6,375,640 B1 | 4/2002 | Teraoka |
| 6,394,983 B1 | 5/2002 | Mayoral et al. |
| 6,485,460 B2 | 11/2002 | Eakins et al. |
| 6,500,155 B2 | 12/2002 | Sasso |
| 6,520,935 B1 | 2/2003 | Jansen et al. |
| 6,540,697 B2 | 4/2003 | Chen |
| 6,565,529 B1 | 5/2003 | Kimber et al. |
| 6,581,792 B1 | 6/2003 | Limanjaya |
| 6,585,691 B1 | 7/2003 | Vitello |
| 6,592,251 B2 | 7/2003 | Edwards et al. |
| 6,666,852 B2 | 12/2003 | Niedospial, Jr. |
| 6,682,798 B1 | 1/2004 | Kiraly |
| 6,726,652 B2 | 4/2004 | Eakins et al. |
| 6,726,672 B1 | 4/2004 | Hanley et al. |
| 6,775,220 B2 | 6/2004 | Castellano et al. |
| 6,764,469 B2 | 7/2004 | Broselow |
| 6,796,586 B2 | 9/2004 | Werth |
| 6,821,268 B2 | 11/2004 | Balestracci |
| D501,549 S | 2/2005 | McAllister et al. |
| 6,921,383 B2 | 7/2005 | Vitello |
| 6,935,560 B2 | 8/2005 | Andreasson et al. |
| 6,942,643 B2 | 9/2005 | Eakins et al. |
| 7,055,273 B2 | 6/2006 | Roshkoff |
| 7,125,397 B2 | 10/2006 | Woehr et al. |
| 7,141,286 B1 | 11/2006 | Kessler et al. |
| 7,175,081 B2 | 2/2007 | Andreasson et al. |
| 7,182,256 B2 | 2/2007 | Andreasson et al. |
| 7,232,066 B2 | 6/2007 | Andreasson et al. |
| 7,240,926 B2 | 7/2007 | Dalle et al. |
| 7,299,981 B2 | 11/2007 | Hickle et al. |
| 7,374,555 B2 | 5/2008 | Heinz et al. |
| 7,404,500 B2 | 7/2008 | Marteau et al. |
| 7,410,803 B2 | 8/2008 | Nollert et al. |
| 7,425,208 B1 | 9/2008 | Vitello |
| 7,437,972 B2 | 10/2008 | Yeager |
| 7,482,166 B2 | 1/2009 | Nollert et al. |
| 7,588,563 B2 | 9/2009 | Guala |
| 7,594,681 B2 | 9/2009 | DeCarlo |
| 7,608,057 B2 | 10/2009 | Woehr et al. |
| 7,611,487 B2 | 11/2009 | Woehr et al. |
| 7,632,244 B2 | 12/2009 | Buehler et al. |

(56) References Cited

U.S. PATENT DOCUMENTS

| | | | |
|---|---|---|---|
| D608,900 S | 1/2010 | Giraud et al. |
| 7,641,636 B2 | 1/2010 | Moesli et al. |
| D612,939 S | 3/2010 | Boone, III et al. |
| 7,681,606 B2 | 3/2010 | Khan et al. |
| 7,698,180 B2 | 4/2010 | Fago et al. |
| 7,735,664 B1 | 6/2010 | Peters et al. |
| 7,748,892 B2 | 7/2010 | McCoy |
| 7,762,988 B1 | 7/2010 | Vitello |
| 7,766,919 B2 | 8/2010 | Delmotte |
| 7,802,313 B2 | 9/2010 | Czajka |
| 7,918,830 B2 | 4/2011 | Langan et al. |
| 7,922,213 B2 | 4/2011 | Werth |
| 8,034,041 B2 | 10/2011 | Domkowski |
| 8,079,518 B2 | 12/2011 | Turner et al. |
| 8,091,727 B2 | 1/2012 | Domkowski |
| 8,118,788 B2 | 2/2012 | Frezza |
| 8,137,324 B2 | 3/2012 | Bobst |
| 8,140,349 B2 | 3/2012 | Hanson et al. |
| 8,252,247 B2 | 8/2012 | Ferlic |
| 8,257,286 B2 | 9/2012 | Meyer et al. |
| 8,328,082 B1 | 12/2012 | Bochenko et al. |
| 8,348,895 B1 | 1/2013 | Vitello |
| 8,353,869 B2 | 1/2013 | Ranalletta et al. |
| 8,443,999 B1 | 5/2013 | Reinders |
| D684,057 S | 6/2013 | Kwon |
| 8,512,277 B2 | 8/2013 | Del Vecchio |
| 8,556,074 B2 | 10/2013 | Turner et al. |
| 8,579,116 B2 | 11/2013 | Pether et al. |
| 8,591,462 B1 | 11/2013 | Vitello |
| 8,597,255 B2 | 12/2013 | Emmott et al. |
| 8,597,271 B2 | 12/2013 | Langan et al. |
| 8,616,413 B2 | 12/2013 | Koyama |
| D701,304 S | 3/2014 | Lair et al. |
| 8,672,902 B2 | 3/2014 | Ruan et al. |
| 8,702,674 B2 | 4/2014 | Bochenko |
| 8,777,910 B2 | 7/2014 | Bauss et al. |
| 8,777,930 B2 | 7/2014 | Swisher et al. |
| 8,852,561 B2 | 10/2014 | Wagner et al. |
| 8,864,021 B1 * | 10/2014 | Vitello ............... A61M 5/5086 235/375 |
| 8,864,707 B1 | 10/2014 | Vitello |
| 8,864,708 B1 | 10/2014 | Vitello |
| 8,911,424 B2 | 12/2014 | Weadock et al. |
| 8,945,082 B2 | 2/2015 | Geiger et al. |
| 9,082,157 B2 | 7/2015 | Gibson |
| 9,101,534 B2 | 8/2015 | Bochenko |
| D738,495 S | 9/2015 | Strong et al. |
| D743,019 S | 11/2015 | Schultz |
| 9,199,042 B2 | 12/2015 | Farrar et al. |
| 9,199,749 B1 | 12/2015 | Vitello |
| 9,220,486 B2 | 12/2015 | Schweiss et al. |
| 9,220,577 B2 | 12/2015 | Jessop et al. |
| 9,227,019 B2 | 1/2016 | Swift et al. |
| D750,228 S | 2/2016 | Strong et al. |
| 9,272,099 B2 | 3/2016 | Limaye et al. |
| 9,311,592 B1 | 4/2016 | Vitello |
| D756,777 S | 5/2016 | Berge et al. |
| 9,336,669 B2 | 5/2016 | Bowden et al. |
| D759,486 S | 6/2016 | Ingram et al. |
| D760,384 S | 6/2016 | Niunoya et al. |
| D760,902 S | 7/2016 | Persson |
| 9,402,967 B1 | 8/2016 | Vitello |
| 9,427,715 B2 | 8/2016 | Palazzolo et al. |
| 9,433,768 B2 | 9/2016 | Tekeste et al. |
| 9,463,310 B1 | 10/2016 | Vitello |
| D773,043 S | 11/2016 | Insgram et al. |
| D777,903 S | 3/2017 | Schultz |
| 9,662,456 B2 | 5/2017 | Woehr |
| D789,529 S | 6/2017 | Davis et al. |
| 9,687,249 B2 | 6/2017 | Hanlon et al. |
| 9,744,304 B2 | 8/2017 | Swift et al. |
| D797,928 S | 9/2017 | Davis et al. |
| D797,929 S | 9/2017 | Davis et al. |
| 9,764,098 B2 | 9/2017 | Hund et al. |
| 9,821,152 B1 | 11/2017 | Vitello et al. |
| D806,241 S | 12/2017 | Swinney et al. |
| D807,503 S | 1/2018 | Davis et al. |
| 9,855,191 B1 | 1/2018 | Vitello |
| D815,945 S | 4/2018 | Fischer et al. |
| 9,987,438 B2 | 6/2018 | Stillson |
| D825,746 S | 8/2018 | Davis et al. |
| 10,039,913 B2 | 8/2018 | Yeh |
| D831,201 S | 10/2018 | Holtz et al. |
| D820,187 S | 11/2018 | Ryan |
| 10,124,122 B2 | 11/2018 | Zenker |
| 10,166,343 B1 | 1/2019 | Hunt et al. |
| 10,166,347 B1 | 1/2019 | Vitello |
| 10,183,129 B1 | 1/2019 | Vitello |
| 10,207,099 B1 | 2/2019 | Vitello |
| D842,464 S | 3/2019 | Davis et al. |
| D847,373 S | 4/2019 | Hurwit et al. |
| 10,300,263 B1 | 5/2019 | Hunt |
| 10,307,548 B1 | 6/2019 | Hunt et al. |
| 10,315,024 B1 | 6/2019 | Vitello et al. |
| 10,376,655 B2 | 8/2019 | Pupke et al. |
| D859,125 S | 9/2019 | Weagle et al. |
| 10,758,684 B1 | 9/2020 | Vitello et al. |
| 2001/0003150 A1 | 6/2001 | Imbert |
| 2001/0034506 A1 | 10/2001 | Hirschman et al. |
| 2001/0056258 A1 | 12/2001 | Evans |
| 2002/0007147 A1 | 1/2002 | Capes et al. |
| 2002/0023409 A1 | 2/2002 | Py |
| 2002/0097396 A1 | 7/2002 | Schafer |
| 2002/0099334 A1 | 7/2002 | Hanson |
| 2002/0101656 A1 | 8/2002 | Blumenthal et al. |
| 2002/0133119 A1 | 9/2002 | Eakins et al. |
| 2003/0055685 A1 | 3/2003 | Cobb et al. |
| 2003/0146617 A1 | 8/2003 | Franko, Sr. |
| 2003/0183547 A1 | 10/2003 | Heyman |
| 2004/0008123 A1 | 1/2004 | Carrender et al. |
| 2004/0064095 A1 | 4/2004 | Vitello |
| 2004/0116858 A1 | 6/2004 | Heinz et al. |
| 2004/0186437 A1 | 9/2004 | Frenette et al. |
| 2004/0225258 A1 | 11/2004 | Balestracci |
| 2005/0146081 A1 | 7/2005 | MacLean et al. |
| 2005/0148941 A1 | 7/2005 | Farrar et al. |
| 2005/0209555 A1 | 9/2005 | Middleton et al. |
| 2006/0084925 A1 | 4/2006 | Ramsahoye |
| 2006/0089601 A1 | 4/2006 | Dionigi |
| 2006/0173415 A1 | 8/2006 | Cummins |
| 2006/0189933 A1 | 8/2006 | Alheidt et al. |
| 2007/0060898 A1 | 3/2007 | Shaughnessy et al. |
| 2007/0106234 A1 | 5/2007 | Klein |
| 2007/0142786 A1 | 6/2007 | Lampropoulos et al. |
| 2007/0191690 A1 | 8/2007 | Hasse et al. |
| 2007/0219503 A1 | 9/2007 | Loop et al. |
| 2007/0257111 A1 | 11/2007 | Ortenzi |
| 2008/0068178 A1 | 3/2008 | Meyer |
| 2008/0097310 A1 | 4/2008 | Buehler et al. |
| 2008/0106388 A1 | 5/2008 | Knight |
| 2008/0140020 A1 | 6/2008 | Shirley |
| 2008/0243088 A1 | 10/2008 | Evans |
| 2008/0306443 A1 | 12/2008 | Neer |
| 2009/0084804 A1 | 4/2009 | Caspary |
| 2009/0099552 A1 | 4/2009 | Levy et al. |
| 2009/0149815 A1 | 6/2009 | Kiel et al. |
| 2009/0326481 A1 | 12/2009 | Swisher et al. |
| 2010/0084403 A1 | 4/2010 | Popish et al. |
| 2010/0126894 A1 | 5/2010 | Koukol et al. |
| 2010/0179822 A1 | 7/2010 | Reppas |
| 2010/0228226 A1 | 9/2010 | Nielsen |
| 2010/0252564 A1 | 10/2010 | Martinez et al. |
| 2010/0283238 A1 | 11/2010 | Deighan et al. |
| 2011/0044850 A1 | 2/2011 | Solomon et al. |
| 2011/0046550 A1 | 2/2011 | Schiller et al. |
| 2011/0046603 A1 | 2/2011 | Felsovalyi et al. |
| 2012/0064515 A2 | 3/2012 | Knapp et al. |
| 2012/0096957 A1 | 4/2012 | Ochman |
| 2012/0110950 A1 | 5/2012 | Schraudolph |
| 2013/0018356 A1 | 1/2013 | Prince et al. |
| 2013/0056130 A1 | 3/2013 | Alpert et al. |
| 2013/0088354 A1 | 4/2013 | Thomas |
| 2013/0237949 A1 | 9/2013 | Miller |
| 2013/0269592 A1 | 10/2013 | Heacock et al. |

(56) References Cited

U.S. PATENT DOCUMENTS

| | | |
|---|---|---|
| 2014/0000781 A1 | 1/2014 | Franko, Jr. |
| 2014/0034536 A1 | 2/2014 | Reinhardt et al. |
| 2014/0069829 A1 | 3/2014 | Evans |
| 2014/0135738 A1 | 5/2014 | Panian |
| 2014/0155868 A1 | 6/2014 | Nelson et al. |
| 2014/0163465 A1 | 6/2014 | Bartlett, II et al. |
| 2014/0257843 A1 | 9/2014 | Adler et al. |
| 2014/0326727 A1 | 11/2014 | Jouin et al. |
| 2014/0353196 A1 | 12/2014 | Key |
| 2015/0182686 A1 | 7/2015 | Okihara |
| 2015/0191633 A1 | 7/2015 | De Boer et al. |
| 2015/0305982 A1 | 10/2015 | Bochenko |
| 2015/0310771 A1 | 10/2015 | Atkinson et al. |
| 2016/0067422 A1 | 3/2016 | Davis et al. |
| 2016/0090456 A1 | 3/2016 | Ishimaru et al. |
| 2016/0144119 A1 | 5/2016 | Limaye et al. |
| 2016/0158110 A1 | 6/2016 | Swisher et al. |
| 2016/0158449 A1 | 6/2016 | Limaye et al. |
| 2016/0176550 A1 | 6/2016 | Vitello et al. |
| 2016/0328586 A1 | 11/2016 | Bowden et al. |
| 2016/0361235 A1 | 12/2016 | Swisher |
| 2016/0367439 A1 | 12/2016 | Davis et al. |
| 2017/0007771 A1 | 1/2017 | Duinat et al. |
| 2017/0014310 A1 | 1/2017 | Hyun et al. |
| 2017/0124289 A1 | 5/2017 | Hasan et al. |
| 2017/0173321 A1 | 6/2017 | Davis et al. |
| 2017/0203086 A1 | 7/2017 | Davis |
| 2017/0319438 A1 | 11/2017 | Davis et al. |
| 2017/0354792 A1 | 12/2017 | Ward |
| 2018/0001540 A1 | 1/2018 | Byun |
| 2018/0078684 A1 | 3/2018 | Peng et al. |
| 2018/0089593 A1 | 3/2018 | Patel et al. |

\* cited by examiner

TAMPER EVIDENT CLOSURE ASSEMBLY

CLAIM OF PRIORITY

This Non-Provisional patent application claims priority to a U.S. provisional patent application having Ser. No. 62/439,538 and a filing date of Dec. 28, 2016, which is incorporated herein by reference in its entirety.

BACKGROUND OF THE INVENTION

Field of the Invention

The present invention is directed to a tamper evident closure structured for attachment to a connector associated with a medical device and includes an end cap and a tip cap. Rotation of the tip cap, in a single direction, within the end cap, causes the disconnection of an indicator member from the end cap and provides an indication of tampering. A cover is connected to the end cap and includes an access opening dimensioned to allow insertion of the connector therethrough, into attachment with the tip cap, while preventing insertion of an instrument or tool into the end cap through the access opening, for purposes of defeating the tamper evident capabilities of the closure.

Description of the Related Art

In the medical field, it is a relatively common procedure to administer fluids to a patient by syringes, intravenous (IV) infusion devices, medical tubing, etc. and such medical devices are useful in helping the treatment of a number of medical conditions. Such treatment may involve administering a variety of fluids and/or medicines to a patient utilizing such medical devices over a prescribed period of time and in controlled amounts.

By way of example, a conventional IV administration assembly typically includes a reservoir or container, in the form of a bottle or more commonly, a flexible material bag, suspended on a pole or like support structure located substantially adjacent to the patient being treated. In addition, various fluids or medicine can be administered to the patient by means of fluid flowing from the supported and elevated IV bottle or bag to the patient within elongated, flexible medical tubing connected at a proximal end to the IV bottle or bag, and at the other distal end, connected intravenously to the patient by way of a catheter or like structure. The IV bag and/or delivery tube is also structured to connect at one end to, or to be interconnected with, an appropriate connector. In turn, the connector of the tube or other medical device is disposed in fluid communication with the contents of the IV bag.

Somewhat similarly, a pre-filled syringe containing medicine or other fluid which is to be administered to a patient typically includes a nozzle or discharge port. In order to prevent fluid flow through the discharge port, a connector is attached thereto in fluid flow restricting relation to the contents of the pre-filled syringe.

Connectors of the type referred to herein, used in association with a pre-filled syringe, IV bottle or IV bag, or other medical device/container may be in the form of a male or female connector attached to the discharge port of the syringe, IV bag, or other medical container/device and disposed in fluid communication with the contents thereof. An appropriate male or female connector may be, but is not limited to, a luer connector, which at least partially defines, a "luer lock" connector assembly, as is well known in the medical profession. The connector associated with the medical device is specifically structured to be attached to an appropriately and cooperatively structured connector in a manner which establishes fluid communication with contents of the prefilled syringe, IV container or other medical device, while facilitating a flow of the fluid contents from the medical device and/or container at a site of the administration to a patient. As a result, fluid flow between the patient and the interior of the medical device and/or container is established. Various types of valves and/or flow regulating devices may be operatively associated with the medical device and or container to regulate the amount or rate of fluid delivery to the patient during the administration procedure.

In periods of non-use or temporary storage of such medical devices and/or containers, it is important to maintain them in a closed and fluid sealed condition in order to maintain the sterility as well as the integrity of the contents of the medical device prior to use. However, known or conventional closure assemblies for such purposes often make it difficult to sufficiently maintain the integrity of the closure assembly in place on the connector associated with the medical device, even though this is necessary to prevent tampering or at least to indicate tampering or an attempt to access the contents of the medical device and/or container. Moreover, tampering or access to the contents of a syringe, IV bag, etc. may be attempted by removal of the closure or the connector, or in the alternative, by using an instrument or tool to access the closure in an attempt to defeat any tamper evidencing capabilities.

Therefore, there is a need in the medical field and related art for an efficient, effective and easily applied tamper evident closure assembly which provides a clear indication that the integrity of the contents of the medical device and/or container is maintained, which should include the integrity of any closure assembly itself. Accordingly, if any such proposed or improved closure assembly were developed, it would preferably provide a visual indication that any tampering has occurred, even if an attempt to access the content via the closure assembly is made by using an instrument, tool, etc. to enter the interior of the closure and disengage components or render them or portions of them inoperative.

In addition, if any such closure assembly were developed, it would preferably include features to enable its use with different types of connectors for different types of medical devices such as, but not limited to, those commonly used in the medical profession. Finally, it would also be preferable if any such closure assembly were developed so as to also operate to include a clear, visually observable signal or indication that either the medical device, connector and/or closure assembly has been tampered with or accessed. As a result, unauthorized access to the medicine or other contents of the medical device with which any such a proposed closure assembly is used, would be clearly and visually apparent.

SUMMARY OF THE INVENTION

The present invention is directed to a tamper evident closure structured to be attached to the connector of a medical device or container such as, but not limited to, a syringe, IV bag, IV bottle, medical tubing associated therewith, etc. Moreover, the structural and operative features of the tamper evident closure according to the present invention restrict and/or render obvious attempted access to the attached medical device by providing at least a visual indication when such access to the medical device, or its contents has been attempted. Additional structural and operational features of one or more embodiments of the tamper evident closure include a prevention of access to the interior thereof, by an instrument, tool, etc., which may be used in an effort to defeat the tamper evident capabilities and/or features of the closure.

Accordingly, one or more preferred embodiments of the tamper evident closure include an end cap generally in the form of a sleeve having an at least partially hollow interior and including a closed end and an oppositely disposed open end. In addition, a tip cap is movably and removably disposed in an operative position within the interior of the end cap. Further, an indicator member, preferably in the form of an indicator ring is disposed within the interior of the end cap, preferably in surrounding relation to a portion of the tip cap.

Moreover, the indicator ring is removably connected to an interior of the end cap, such as to an interior sidewall surface thereof, by at least one frangible member. The tamper evident closure also includes a unidirectional or one-way rotational drive, operative to allow rotation of the tip cap, within the end cap, in a single direction, such as a counter-clockwise direction. In contrast, the one-way rotational drive is also operative to prevent rotation of the tip cap, within the end cap, in the opposite direction, such as in the clockwise direction. As a result, a connector of a prefilled syringe, IV bag or other medical device can be "threaded" or otherwise rotationally attached to the tip cap, while the tip cap is disposed within the interior of the end cap in a fixed orientation. Such threaded engagement will be accomplished by rotating the connector of the medical device in a clockwise direction. As indicated, operative features of the one-way rotational drive will prevent rotation of the tip cap, within the end cap, in the clockwise direction. As a result, a threaded attachment between the connector of the medical device and the tip cap can be effectively accomplished.

However, attempts to access the medical device, and/or its contents by "unthreading" the connector of the medical device from the tip cap will result in a counter-clockwise rotation of the connector and medical device, and a concurrent counter-clockwise rotation of the tip cap. As indicated, the one-way rotational drive will allow and facilitate continuous rotation of the tip cap, in a counterclockwise direction, within the interior of the end cap. Accordingly, the "unthreading" of the connector of the medical device from the tip cap will be prevented, since the connector/medical device and the tip cap will continuously rotate together in the counter-clockwise direction. However, as set forth in greater detail hereinafter attempts to unthreaded the connector of the medical device from the tip cap will result in a disconnection of the indicator member or ring from the interior surface portions of the end cap or sleeve, due to interaction of the drive segments associated with the one-way rotational drive assembly.

In more specific terms and as generally indicated, the indicator member, preferably in the form of an indicator ring, is removably attached to the interior of the end cap by one or more frangible members. As a result, the allowed rotation of the tip cap in the counter-clockwise direction will cause a simultaneous forced rotation of the indicator member or ring with the tip cap. Such a forced, counter-clockwise rotation of the indicator member will result in a breakage of the at least one frangible member interconnecting the indicator member to the interior of the end cap. However, the indicator member/ring will remain attached to the tip cap and be removable with the tip cap, when the tip cap and attached connector of the medical device are concurrently removed from the interior of the end cap. Further, the detachment of the indicator ring from the interior of the end cap and its presence on the exterior of the tip cap, when both are concurrently removed from the end cap, will provide a clear visual indication that tampering and attempted access, either authorized or unauthorized, to the medical device has occurred.

Yet additional features of the tamper evident closure include the ability to prevent access to the interior of the end cap, by a tool or instrument, in an attempt to overcome the tamper evident capabilities of the closure assembly. More specifically, one or more embodiments of the tamper evident closure includes a cover, having an access opening, connected to the open end of the end cap. As such, the cover at least partially restricts access to the interior of the end cap, except by the connector of the medical device passing through the aforementioned access opening. Therefore, the access opening is structured to include "cooperative dimensioning" with the connector of the medical device to which the tip cap is attached. In even more specific terms, the inner periphery of the access opening is correspondingly dimensioned to outer surface of the connector of the medical device. As such, the passage of the connector through the access opening is facilitated to accomplish its attachment to the tip cap. Such attachment may be accomplished by a threaded interconnection. However, the size or diameter of the access opening is such as to prevent passage therethrough of the tip cap from the interior of the end cap outwardly through the cover.

Accordingly, the above-noted "cooperative dimensioning" of the access opening allows and facilitates the passage there-through of the connector into direct alignment and/or access with the tip cap However, the inner periphery of the access opening is cooperatively and correspondingly dimensioned with the outer surface of the connector. As a result, the passage and placement of the connector through the access opening will result in an engaging relation between the inner periphery of the access opening and the exterior surface of the connector. Such engagement will result in an effective closing of the access opening due to the fact that the inner periphery of the access opening engages the outer surface of the connector continuously along the entirety of the inner periphery. Therefore and as indicated, the access opening will be closed and there will be no spacing or open area between the inner periphery of the access opening and the outer surface. Any attempts to access the interior of the end cap or sleeve, through the access opening, utilizing an instrument, tool, etc., for purposes of defeating the above-noted tamper evident capabilities, will be prevented. In addition, as the connector is threaded onto the tip cap, the connector of the medical device will be drawn further into the interior of the end cap, through the access opening. This threaded attachment, as indicated above, will in effect tighten the engagement between the inner periphery of the access opening and the outer surface of the connector and may result in a "friction fit" there between.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 3:
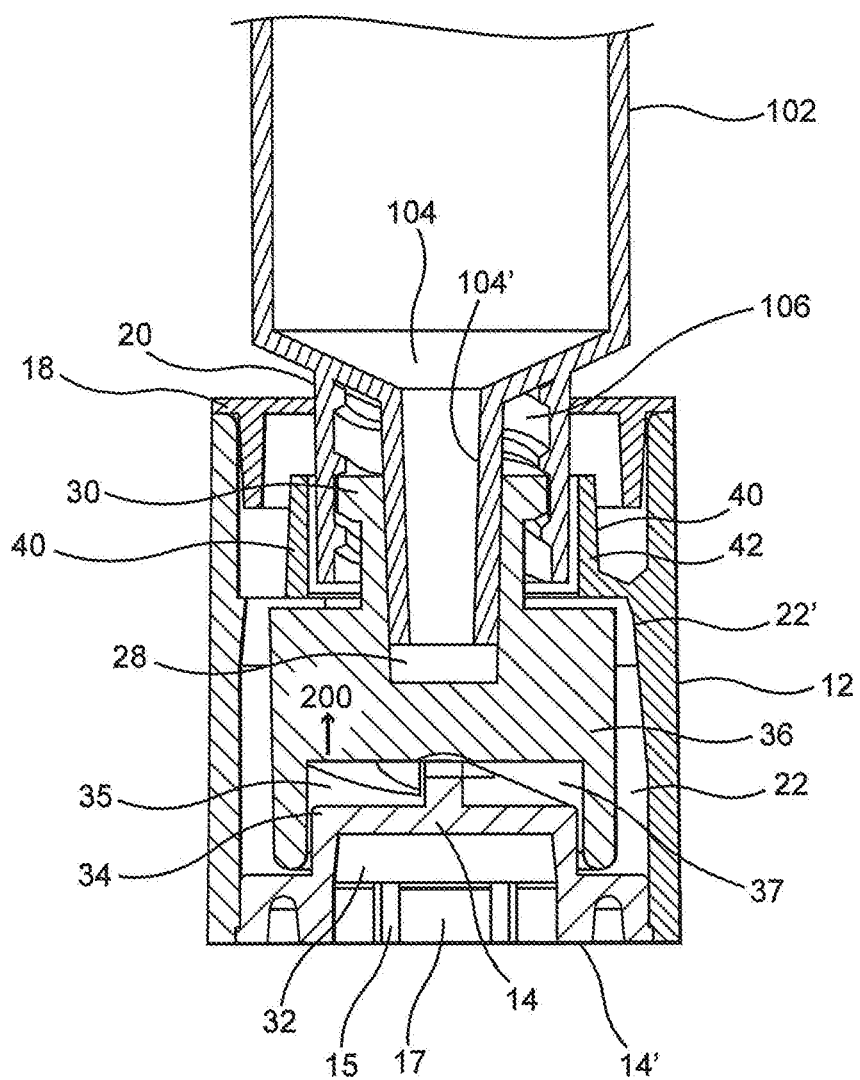
FIG. 3 is an interior sectional view of the tamper evident closure of the embodiment of FIGS. 1 and 2 attached to a connector of a medical device.

As represented in the accompanying drawings, the present invention is directed to a tamper evident closure generally indicated as 10 and structured to be attached to a connector 100 of any one of a variety of different medical devices 102. As represented in FIG. 3, the medical device 102 is illustrated in the form of a syringe and/or a pre-filled syringe having a medicine already contained within it. However, it is emphasized that the structural and operative features associated with the tamper evident closure 10 make it adaptable for connection to different medical devices including, but not limited to, a syringe 102, but also to an IV bag, medical tubing, tube set, etc.

The structural features of the tamper evident closure 10 include an outer sleeve or end cap 12 having a closed, and preferably integrally formed, end 14 and an oppositely disposed open end 16. As will be explained in greater detail hereinafter, a cover generally indicated as 18 is connected in overlying, at least partially covering and closing relation to the open end 16 and further includes an access opening 20. The interior 22 of the sleeve or end cap 12 is at least partially hollow and is dimensioned and configured to retain a tip cap 24 in an operative position therein. Such operative position is represented in both FIGS. 2 and 3 and will be further defined hereinafter with regard to the additional structural components of the tamper evident closure 10, as well as the operative features thereof.

Figure 1:
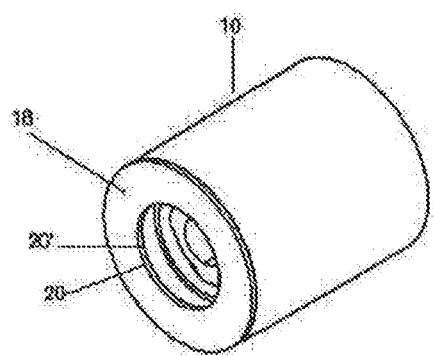
FIG. 1 is a perspective view of the tamper evident closure of the present invention in an assembled form.
Figure 2:
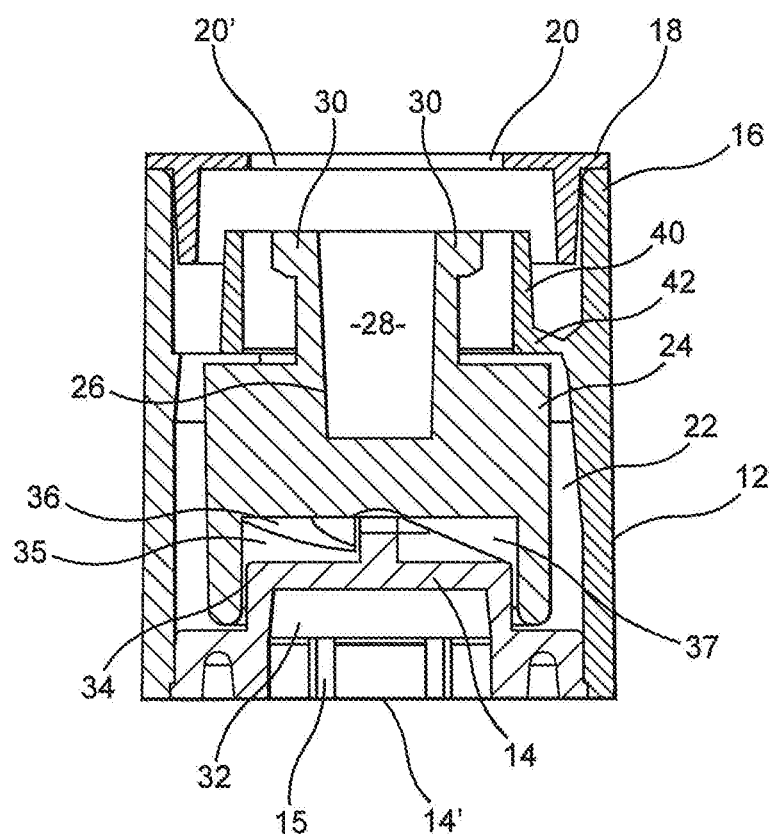
FIG. 2 is an interior sectional view of the tamper evident closure of the embodiment of FIG. 1.

As illustrated in FIG. 2, the tip cap 24 also includes a flow controller 26 disposed and structured to operatively interact with the discharge port 104 or nozzle 104' of the syringe 102 or other medical device. In the embodiment represented, the flow controller 26 and the associated portion of the tip cap 24 may be accurately described as having the configuration of a "female connector". As such, the flow controller 26 includes an open receiving chamber 28 dimensioned to receive the nozzle 104' therein. Therefore, when the flow controller 26 and/or the receiving chamber 28 are disposed in receiving relation to the discharge port 104 and nozzle 104' of the connector 100 and medical device 102, the flow controller 26 is disposed in a flow restricting relation with the discharge port 104 and nozzle 104'. Such a flow restricting relation is defined as preventing or at least restricting fluid from passing through the connector 100 and more specifically, the discharge port 104 and/or nozzle 104'.

In order to establish and maintain the aforementioned flow restricting relation, the female connector configuration of the flow controller 26 and tip cap 24 are structured for attachment to the connector 100, as clearly represented in FIG. 3. Such attachment may be accomplished by a threaded connection between the outwardly extending ears, ribs or thread segments 30 on the exterior of the flow controller 26 and the interior threaded surface 106 within the connector 100. As should be apparent, such a threaded connection would involve passage of the connector 100 through the access opening 20 of the cover 18. Assuming a "right-hand" threaded configuration, the medical device 102 is then rotated in a clockwise direction by exerting a rotational force thereon. As such, threaded engagement between the thread segments 30 and the interior threaded surface 106 will occur.

Facilitating such threaded engagement between the medical device 102 and the tip cap 24 is the interaction between the tip cap 24 and a one-way rotational drive 32. More specifically, the tip cap 24 will be temporarily maintained in a fixed orientation due to interaction of the one-way rotational drive 32 connected to both the closed end 14 and a corresponding interior surface of the tip cap 24. In more specific terms, the one-way drive assembly 32 comprises at least two drive segments 34 and 36, each formed on a different one of the closed end 14 of the sleeve or end cap 12 and the tip cap 24. More specifically, drive segment 34 may be disposed on the interior surface of the closed end 14 and the other drive segment 36 may be formed on the lower, bottom, at least partially interior surface of the tip cap 24, as clearly represented in FIG. 3. Further, the one-way drive assembly 32 may be in the form of a "ramp and cliff" drive assembly. As such the at least two drive segments 34 and 36 are cooperatively dimensioned and configured to form the aforementioned "ramps" 35, 37 and "cliffs" 39, as explained in greater detail hereinafter, with specific reference to FIGS. 4A and 4B.

Therefore, one operative feature of the tamper evident closure 10 of the present invention is the structuring of the one-way rotational drive 32 including the at least two drive segments 34 and 36 to permit rotation of the tip cap 24 within the interior 22 of the sleeve or end cap 12 in only a single direction. However, and as set forth above, the structural and operative features of the one-way rotational drive 32 also prevent rotation of the tip cap 24 within the interior 22 of the end cap 12 in an opposite direction. Therefore, in order to facilitate a threaded attachment of the threaded interior surface 106 of the connector 100 with the thread segments 30 of the flow controller 26 and/or tip cap 24, the single allowed direction of rotation of the tip cap is in a counter-clockwise rotational direction, while the tip cap 24 is prevented from rotating in a clockwise direction. When an attempt is made to rotate the tip cap 24 in a clockwise direction, an interruptive, abutting engagement between the cliff segments 39 of each of the drive segments 34 and 36 will occur, and thereby, prevent rotation of the tip cap 24 in the clockwise direction. This will allow a temporary "fixed" orientation of the tip cap 24 within the interior 22, while a clockwise, rotational force is being applied to the device 102. As indicated, the clockwise rotation of the medical device 102 will accomplish the threaded engagement between the threaded surface 106 and the thread segments 30 due, at least in part, to the fact that the tip cap 24 is temporarily disposed in the fixed orientation.

In cooperation therewith, the tamper evident closure 10 also includes an indicator member 40 which is preferably in the form of an indicator ring, as illustrated in FIGS. 2 and 3. The indicator member or ring 40 is removably connected to an internal surface of the end cap 12, such as at 22', by at least one frangible member 42. For purposes of clarity, only a single frangible member 42 is represented in the accompanying Figures. However, as a practical matter, a plurality of such frangible members 42 may be disposed in spaced relation to one another and collectively, in surrounding relation to the indicator member 40. As indicated, each of the one or more frangible members 42 are disposed in interconnecting relation between exterior portions of the indicator member or ring 40 and the interior side wall or other appropriate interior surface 22' of the end cap or sleeve 12.

With additional reference to the one-way rotational drive assembly 32, the at least two drive segments 34 and 36 are cooperatively disposed and configured to define a movable and/or sliding mating engagement with one another when the tip cap 24 is rotated in a counter-clockwise direction, such as when an attempt is made to "unthread" or "unscrew" the medical device 102 from its attachment with the tip cap 24. Moreover, the size, configuration and disposition of the drive segments 34 and 36 are such as to cause an outwardly or upwardly movement or disposition of the tip cap 24, as schematically represented by directional arrow 200 in FIG. 3, away from the closed end 14 and towards and into "disconnecting engagement" with the indicator member or ring 40. Such a disconnecting engagement will result in a breakage of the one or more frangible members 42.

Figure 4A:
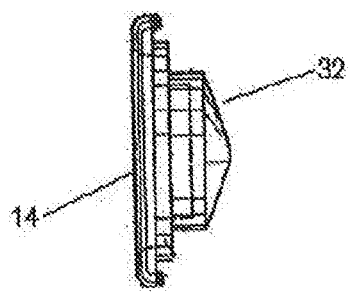
FIG. 4A is a detail side view of at least one drive segment of a one-way rotational drive, represented in an assembled form in the embodiment of the tamper evident closure of FIGS. 1-3.
Figure 4B:
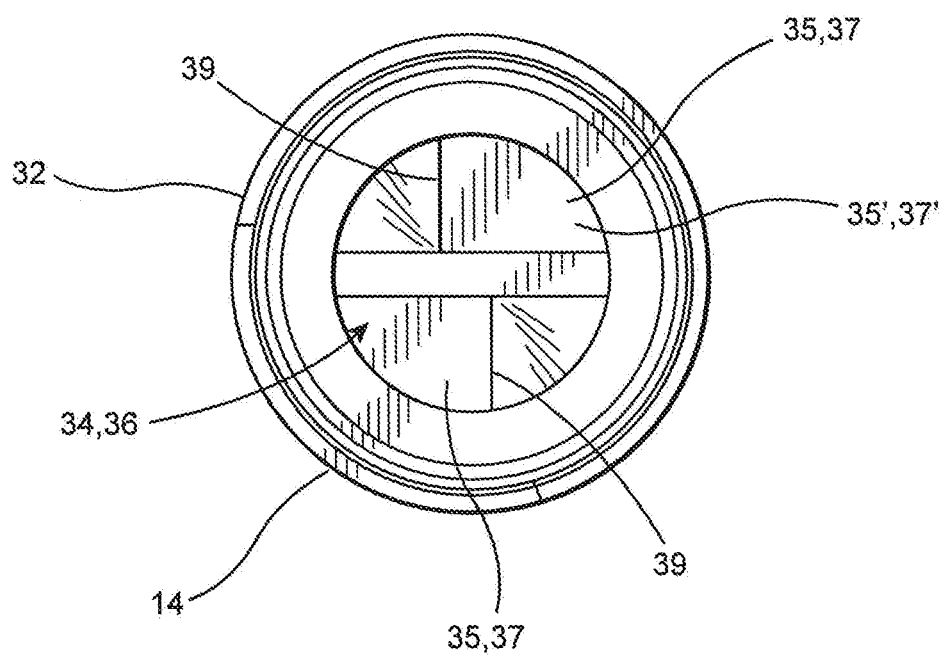
FIG. 4B is an interior plan view of the embodiment of FIG. 4A.

With reference now to FIGS. 4A-4B, certain structural details of the one-way rotational drive 32 are represented. For purposes of clarity, only a single drive segment 34, formed on the interior surface of the closed end 14 of the end cap 12, is presented. However, it is emphasized that the configuration and overall structure of the drive segment 36 located on an inner surface of the tip cap 24, as represented in FIGS. 2 and 3, are the structural equivalent of the drive segment 34, represented in FIGS. 4A and 4B. More specifically, each of the drive segments 34 and 36 include at least one, but more practically, a plurality of spaced-apart, sloped ramps 35, 37 terminating in a cliff structure as at 39. Therefore, when an attempt is made to rotate the tip cap 24 in a clockwise direction, the cliff structures or portions 39 of each of the drive segments 34 and 36 will be disposed in engaging, abutting relation to one another. As a result, rotation of the tip cap 24 in the clockwise direction will be prevented. This, in turn, will allow the threaded attachment of the connector 100 onto the thread segments 30, as described above.

In contrast, attempted rotation of the tip cap 24 in the counter-clockwise direction will result in a mating, sliding engagement of the outwardly sloped ramp segments or portions 35, 37 of each of the drive segments 34 and 36. That is, because the ramp segments 35, 37 have an upwardly or outwardly sloped configuration extending from one end 35' 37' to the corresponding cliff segment 39, a moving, sliding, mating engagement will occur between such ramp segments 35, 37 formed on the different drive segments 34 and 36. Such sliding, mating engagement will result in a forced upwardly or outwardly positioning, as at 200 (See FIG. 3), of the tip cap 24 into the above noted "disconnecting engagement" with the adjacently positioned indicator member or ring 40.

Therefore, and for purposes of clarification, an attempt to unthread or unscrew the medical device 102 from the tip cap 24 will result in a counter-clockwise directional force being exerted on the tip cap 24 due to its attachment with the connector 100, as set forth above. Such a counter-clockwise rotation of the tip cap 24 will result in movable, sliding, mating engagement between the ramp segments 35, 37 of each of the drive segments 34 and 36. Due to the generally upwardly or outwardly sloped configuration of the ramp segments 35 and 37, an outward or upward raising or positioning of the tip cap 24 will occur, as schematically represented by directional arrow 200 shown in FIG. 3. Any such upward or outward forced positioning 200 of the tip cap 24 will result in the tip cap 24 being forced into engagement and thereby establishing or defining the aforementioned "disconnecting engagement" with the adjacently positioned indicator member or ring 40. Due to the size, configuration and overall structure of the drive segments 34 and 36, including the ramp segments 35 and 37 and the cliff segments 39, the force exerted on the indicator member or ring 40 upon the occurrence of such disconnecting engagement of the tip cap 24 therewith, will result in a breakage of the one or more frangible members 42. As a result, the indicator member or ring 40 will become disconnected from the interior surface of the sleeve or end cap 12.

When so disconnected from an interior surface of the end cap or sleeve 12, indicator 40 will remain in surrounding relation to the flow controller 26 and the connector 100 attached to the tip cap 24. Further, such disconnection will provide a clear indication of attempted access or "tampering" to the extent that it will be evident that the medical device 102 was attempted to be removed, by an unthreading of the connector 100 from the tip cap 24 and the closure 10. Further, if the tip cap 24 is removed from the interior 22 of the sleeve or end cap 12, while remaining attached to the medical device 102, the indicator member or ring 40 will remain in surrounding relation to the connector 100. As a result, a clear visual indication of tampering or attempted access, either authorized or unauthorized will be evident.

Yet additional structural and operative features of the tamper evident closure 10 of the present invention are directed to preventing attempts to defeat the tamper evident capabilities of the closure 10, as set forth above. More specifically, the tamper evident closure 10 prevents or at least significantly restricts access to the interior of the end cap or sleeve 12 by a tool, instrument, etc. As set forth above, the cover 18 is disposed in overlying at least partially covering relation to the open end 16 of the end cap 12. As also indicated, the cover 18 includes an access opening 20 which includes "cooperative dimensioning" with at least the outer surface 100' of the connector 100 of the medical device 102 to which the tamper evident closure 10 is attached.

Accordingly, such cooperative dimensioning of the access opening 20 allows and facilitates the passage there-through of the connector 100 into direct alignment and or access with the flow controller 26 and the thread segments 30 associated therewith. However, the inner periphery 20' of the access opening 20 is cooperatively and correspondingly dimensioned with the outer surface 100' of the connector 100. As a result, the passage and placement of the connector 100 through the access opening 20 will result in an engaging relation between the inner periphery 20' and the exterior surface 100'. Such engagement will result in an effective closing of the access opening 20, as clearly represented in FIG. 3, due to the fact that the inner periphery 20' engages the outer surface 100' continuously along the entirety of the inner periphery 20'. Therefore, and as indicated, the access opening 20 will be closed and there will be extremely little or preferably no spacing or open area between the inner periphery 20' and the outer surface 100'. Any attempts to access the interior of the end cap or sleeve 12 through the access opening 20, utilizing an instrument, tool, etc., for purposes of defeating the above-noted tamper evident capabilities, will be prevented. In addition, as the connector 100 is threaded onto the tip cap 24, the connector will be drawn further through the access opening 20 into the interior of the end cap or sleeve 12. This threaded attachment, as indicated above, will in effect tighten the engagement between the inner periphery 20' and the outer surface 100' and may result in a "friction fit".

In accordance with the above noted structural and operative features, authorized or unauthorized forced removal of the tip cap 24, while still being attached to the connector 100, may be accomplished by exerting an oppositely directed pulling force on either the medical device 102, as schematically represented as 300, or on the tamper evident closure 10, or both. Such a pulling force will result in the unattached, disconnected indicator ring 40 remaining in surrounding relation to the attached connector 100 and tip cap 24 as they concurrently exit the interior 22 of the end cap or sleeve 12. In addition, the cover 18 will also remain in surrounding relation to the connector 100 by virtue of its forced removal from the open end 16 of the end cap or sleeve 12.

As also clearly represented in FIGS. 2 and 3, the aforementioned "cooperative dimensioning" may be further demonstrated by the diameter of the access opening 20 being smaller or lesser than the diameter of the indicator member or ring 40, as well as smaller or lesser than a major or largest diameter of the tip cap 24. As a result, passage of the indicator member or ring 40 or the tip cap 24 through the access opening 20 is prevented. As a result, concurrent removal of the tip cap 24 and indicator member or ring 40, while still being attached to the connector 100 of the medical device 102 is accomplished by the aforementioned pulling force 300 being exerted oppositely on the medical device 102 and/or the tamper evident closure 10.

As disclosed in detail in what may be considered related intellectual property rights hereto, namely, U.S. Pat. Nos. 8,591,462 and 9,199,749, issued respectively on Nov. 26, 2013 and Dec. 1, 2015 to Vitello, the exterior 14' of the integrally formed, closed end 14 may include a plurality of projections 15, shown in FIGS. 2 and 3, formed at least partially on the interior peripheral surfaces of a corresponding recess 17. The plurality of projections 15 may vary in number and placement, but would be cooperatively disposed, structured and dimensioned to interact with correspondingly structured and dimensioned projections of outwardly protruding connectors, which may be part of a package or packaging structure for a plurality of tamper evident closures 10. Reference is specifically, but not exclusively made to FIGS. 8-10 and 11-14, of the above noted patents.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A tamper evident closure structured for attachment to a connector of a medical device, said tamper evident closure comprising:
   an end cap having an open end,
   a tip cap movably and removably disposed within said end cap in an operative position,
   a cover removably connected to said end cap in at least partially covering relation to said open end,
   said cover including an access opening, said access opening including cooperative dimensioning with the connector of the medical device,
   said cooperative dimensioning comprising passage of the connector through said access opening into attachment with said tip cap,
   said cooperative dimensioning preventative of passage of said tip cap through said access opening to an exterior of said and end cap,
   said cooperative dimensioning further comprising engagement of an inner periphery of said access opening with an outer surface of the connector,
   said engagement between said inner periphery of said access opening defining a closure of said access opening; said closure of said access opening preventative of further access to an interior of said end cap through said access opening,
   a one-way rotational drive disposed on said tip cap and said end cap, said one-way rotational drive configured to define rotation of said tip cap in a single direction, concurrent to said operative position,
   an indicator member disposed within and removably connected to said end cap in adjacent relation to said tip cap, and
   said one-way rotational drive structured to dispose said tip cap into disconnecting engagement with said indicator member, concurrent to rotation of said tip cap in said single direction, and
   said disconnecting engagement comprising a detachment of said indicator member from an interior of said end cap.

2. The tamper evident closure as recited in claim 1 further comprising at least one frangible connector member removably connecting said indicator member to an interior wall surface of said end cap.

3. The tamper evident closure as recited in claim 2 wherein said disconnecting engagement of said tip cap with said indicator member comprises a breakage of said at least one frangible member and a disconnection of said indicator member from said interior surface.

4. The tamper evident closure as recited in claim 1 wherein said one-way rotational drive includes first and second drive segments each disposed on a different one of said tip cap and said end cap in mating relation to one another, said first and second drive segments cooperatively disposed and configured to define said single direction of rotation of said tip cap within said end cap, when said tip cap is in said operative position.

5. The tamper evident closure as recited in claim 1 wherein said indicator member comprises an indicator ring; said indicator ring disposed adjacent and in surrounding relation to said tip cap and between said tip cap and said cover, when said tip cap is in said operative position.

6. The tamper evident closure as recited in claim 1 wherein said tip cap further comprises a flow controller, said operative position comprising said flow controller disposed in substantially axially aligned relation to said access opening and in accessible relation to the connector disposed within said access opening.

7. The tamper evident closure as recited in claim 6 wherein said flow controller is disposed and structured to restrict fluid flow through the connector of the medical device, concurrent to attachment of the connector and said tip cap.

8. The tamper evident closure as recited in claim 1 wherein said access opening includes a diameter having a dimension substantially corresponding to a dimension of an outer diameter of the connector of the medical device.

9. The tamper evident closure as recited in claim 8 wherein said corresponding dimension of said diameter of said access opening defines said engagement between an entirety of said inner periphery of said access opening and the outer surface of the connector.

10. The tamper evident closure as recited in claim 9 wherein said diameter of said access opening includes a lesser dimension than a major outer diameter of said tip cap.

11. The tamper evident closure as recited in claim 1 wherein said access opening includes a diameter having a lesser dimension than a major outer diameter of said tip cap.

12. A tamper evident closure structured for attachment to a connector of a medical device, said tamper evident closure comprising:
    an end cap and a tip cap; said tip cap movably and removably disposed within said end cap in an operative position,
    an indicator member attached to said tip cap and removably connected to said end cap,
    a cover removably connected to said end cap and including an access opening, said access opening including cooperative dimensioning with the connector of the medical device,
    said cooperative dimensioning comprising disposition of the connector through said access opening into attachment with said tip cap and into concurrent engagement with an inner periphery of said access opening,
    said engagement between said inner periphery of said access opening defining a closure of said access opening; said closure of said access opening preventative of further access to an interior of said end cap through said access opening,
    a one-way rotational drive disposed on said tip cap and said end cap, said one-way rotational drive configured to define rotation of said tip cap in a single direction, when said tip cap is in said operative position, and
    said one-way rotational drive structured to dispose said tip cap into disconnecting engagement with said indicator member, concurrently to rotation of said tip cap in said single direction, and
    said disconnecting engagement comprising a disconnection of said indicator member from an interior of said end cap.

13. The tamper evident closure as recited in claim 12 wherein said corresponding dimension of said diameter of said access opening defines said engagement between an entirety of said inner periphery of said access opening and the outer surface of the connector.

14. The tamper evident closure as recited in claim 13 wherein said engagement between an entirety of said inner periphery of said access opening and the outer surface of the connector defines a friction fit therebetween, upon an attachment of the connector with said tip cap.

15. The tamper evident closure as recited in claim 12 further comprising at least one frangible connector member removably connecting said indicator member to an interior surface of said end cap.

16. The tamper evident closure as recited in claim 15 wherein said disconnected engagement of said tip cap further comprises a breakage of said at least one frangible member and a disconnection of said indicator member from said interior surface.

17. The tamper evident closure as recited in claim 12 wherein said indicator member comprises an indicator ring; said indicator ring disposed adjacent and in surrounding relation to said tip cap and between said tip cap and said cover, when said tip cap is in said operative position.

18. The tamper evident closure as recited in claim 12 wherein said one-way rotational drive includes first and second drive segments each disposed on a different one of said tip cap and said end cap in mating relation to one another, said first and second drive segments cooperatively disposed and configured to define said single direction of rotation of said tip cap within said end cap, when said tip cap is in said operative position.

19. The tamper evident closure as recited in claim 12 wherein said diameter of said access opening includes a lesser dimension than a major outside diameter of said tip cap.

20. A tamper evident closure structured for attachment to a connector of a medical device, said tamper evident closure comprising:
    an end cap and a tip cap; said tip cap movably and removably disposed within said end cap in an operative position,
    an indicator member removably connected to said end cap and disposed adjacent and in surrounding relation to said tip cap and between said tip cap and said cover, concurrent to said operative position,
    a one-way rotational drive disposed on said tip cap and said end cap, said one-way rotational drive configured to define rotation of said tip cap in a single direction, when said tip cap is in said operative position,
    said one-way rotational drive includes first and second drive segments each disposed on a different one of said tip cap and said end cap in mating relation to one another,
    said first and second drive segments cooperatively disposed and configured to define said single direction of rotation of said tip cap within said end cap,
    said first and second drive segments cooperatively disposed and configured to dispose said tip cap into a disconnecting engagement with said indicator member, concurrently to rotation of said tip cap in said single direction, and
    said disconnecting engagement comprising a detachment of said indicator member from an interior of said end cap.

* * * * *